United States Patent [19]

Melas et al.

[11] Patent Number: 4,734,514
[45] Date of Patent: Mar. 29, 1988

[54] HYDROCARBON-SUBSTITUTED ANALOGS OF PHOSPHINE AND ARSINE, PARTICULARLY FOR METAL ORGANIC CHEMICAL VAPOR DEPOSITION

[75] Inventors: Andreas A. Melas, Burlington; Benjamin C. Hui, Peabody, both of Mass.; Jorg Lorberth, Weimar-Niederweimar, Fed. Rep. of Germany

[73] Assignee: Morton Thiokol, Inc., Chicago, Ill.

[21] Appl. No.: 828,467

[22] Filed: Feb. 10, 1986

Related U.S. Application Data

[63] Continuation-in-part of Ser. No. 664,645, Oct. 25, 1984.

[51] Int. Cl.$^4$ ................................. C07F 9/70
[52] U.S. Cl. .......................................... 556/70; 568/8; 568/17
[58] Field of Search ......................... 556/70; 568/8, 17

[56] References Cited

U.S. PATENT DOCUMENTS 3,657,298 4/1972 King et al. ........................ 556/70 X

OTHER PUBLICATIONS

Kosolapoff et al, Organic Phosphorus Compounds, vol. 1, pp. 109, 110, 111, 114 to 119 (1972) Wiley-Interscience, N.Y.
Kosolopoff, Organophosphorus Compounds, John Wiley & Sons, Inc., N.Y., pp. 30, 31 (1950).
Doak et al, Organometallic Compounds of Arsenic, Antimony and Bismuth, Wiley-Intersc., N.Y., pp. 126 (1970).
Chemical Abstracts 100 174916b (1984).
Chemical Abstracts 100 121221q (1984).
Chemical Abstracts 86 89943t (1977).
Ashe, et al., Preparation ... Dibismuthines, *Organometallics* 1983, No. 2, p. 1865, Cols. 1-2 (synthesis of benzyldimethylarsine).
Chemical Abstracts 60:14536e.
Chemical Abstracts 62:11405g (1965).
CRC Handbook of Chemistry and Physics, 61st Ed. (1980-81), pp. 640-676.
Organometallic Compounds of Arsenic, Antimony, and Bismuth, pp. 120-127.
Hagihara, et al., Handbook of Organometallic Compounds (1968), pp. 560, 566, 571, 574, 579, 581.
Hagihara, et al. Handbook of Organometallic Compounds (1968), pp. 720-723, 725-726.
Kisolapoff, et al., Organic Phosphorus Compounds, vol. 1, pp. 4-11, 16-27.
Kuech, et al. "Reduction of Background Doping in Metal-Organic Vapor Phase Epitaxy of GaAs using Triethyl Gallium at Low Reactor Pressures", Appl. Phys. Lett., Oct. 15, 1985.
Tzschach, et al., Zur Sythese *Zeitschrift fur Anorganische und Allgemeine Chemie*, Band 326, pp. 280-287 (1964).

Primary Examiner—Paul F. Shaver
Attorney, Agent, or Firm—George Wheeler; Gerald K. White

[57] ABSTRACT

Organometallic compounds having the formulas:

$$X-\underset{\underset{H}{|}}{N}-Y$$

wherein N is selected from phosphorus and arsenic, H is hydride, and X and Y are independently selected from hydride, lower alkyl cyclopentadienyl, and phenyl, except that Y cannot be hydrogen; and

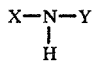

wherein x is an integer from 2 to 4 inclusive, each said R substituent is independently selected from hydride, lower alkyl, phenyl, alkyl-substituted phenyl, cyclopentadienyl, and alkyl-substituted cyclopentadienyl, and M is selected from elements of Groups 2B, 2A, 3A, 5A, and 6A of the Periodic Table, except carbon, nitrogen, oxygen, and sulfur. The use of these compounds in chemical vapor deposition processes and methods for synthesizing these compounds are also disclosed.

43 Claims, 6 Drawing Figures

HYDROCARBON-SUBSTITUTED ANALOGS OF PHOSPHINE AND ARSINE, PARTICULARLY FOR METAL ORGANIC CHEMICAL VAPOR DEPOSITION

CROSS-REFERENCE TO RELATED APPLICATION

This application is a continuation-in-part of U.S. Ser. No. 664,645, filed Oct. 25, 1984 by Hui, Melas, and Lorbeth, now pending.

TECHNICAL FIELD

This invention relates to organometallic compounds comprising elements from Groups 2B, 2A, 3A, 5A, and 6A of the Periodic Table and mixed organic substituents selected from lower alkyl, hydride, phenyl, alkyl-substituted phenyl, cycloalkyl, and alkyl-substituted cycloalkyl; particularly to analogs of arsine ($AsH_3$) and phosphine ($PH_3$) in which one or two of the hydride substituents is replaced by an organic substituent. This invention also relates to metal organic chemical vapor deposition (MOCVD) processes employed in the semiconductor, optical, and optoelectronic industries for doping or coating a suitable substrate.

BACKGROUND ART

MOCVD is a method for depositing dopants or thin metal or metal compound films on a silicon or other substrate. (In the present disclosure "metal" includes all of the elements of Groups 2B, 2A, 3A, 4A, 5A, and 6A of the Periodic Table except carbon, nitrogen, oxygen, and sulfur.) The deposited films can be sources of doping impurities which are driven into the substrate, or the films themselves can have different electrical or optical properties than the substrate. These films are used in laser diodes, solar cells, photocathodes, field effect transistors and other discrete devices, in fiber optic communications, microwave communications, digital audio disc systems, and other advanced semiconductor, optical, and optoelectronic technologies. The properties of the film depend on the deposition conditions and the chemical identity of the deposited film.

A special advantage of MOCVD is that organometallic compounds can be found which have much higher vapor pressures at moderate temperatures than the corresponding metals, and which decompose to release the corresponding metals or form compounds thereof at the 200 to 800 degrees Celsius deposition temperatures which should not be exceeded during fabrication.

Typical apparatus currently in use for MOCVD comprises a bubbler which contains a supply of the organometallic compound chosen for a particular process, a reactor or deposition chamber which contains the substrate on which a film is to be deposited, a source of a carrier gas which is inert to the organometallic compound in the bubbler and either inert or reactive to the compound in the deposition chamber, and optionally sources of other reactants or dopants supplied to the reaction chamber. The bubbler and contents are maintained at a constant and relatively low temperature which typically is above the melting point of the organometallic compound but far below its decomposition temperature. The deposition chamber is typically maintained at a much higher temperature, such as about 200 to 800 degrees Celsius, particularly about 600 to 750 degrees Celsius, at which the organometallic compound readily decomposes to release its constituent metal. To operate the MOCVD apparatus, the carrier gas is introduced into the bubbler under the surface of the organometallic compound. Rising bubbles of the carrier gas provide a large, constant contact surface and thus uniformly vaporize the organometallic compound. The carrier gas and vapor collected in the headspace of the bubbler are continuously directed to the deposition chamber.

While it is possible to vaporize solid sources of arsenic or phosphorus in a bubbler or furnace (see Bhat, cited later), this way of providing arsenic or phosphorus has several disadvantages. First, when a III-V compound such as gallium arsenide is to be deposited the Group III element (here, gallium) is conventionally supplied from an organometallic compound such as trimethylgallium. The source of the Group V element should include hydride substituents so that monatomic hydrogen will be formed when the hydride decomposes in the deposition chamber. The monatomic hydrogen thus formed will react with the organic radicals (methyl radicals, in the case of trimethylgallium) formed by decomposition of the Group V source in the deposition chamber to form gaseous waste (here, methane gas), allowing the organic constituents to be removed from the site of deposition. For this reason, in prior practice a large excess of Group V hydride (here, arsine) has been supplied to ensure thorough removal of organic constituents. Elemental arsenic supplied to the deposition chamber would include no hydride substituents, and thus the resulting film would be contaminated with carbon from the Group III source.

Second, it is difficult to control the rate of vaporization of such solid sources because the surface area of a solid exposed to the carrier gas changes as vaporization proceeds. In contrast, a liquid contained in a bubbler with substantially vertical walls presents the same surface area to the carrier gas so long as the flow and bubble size of the carrier gas remains steady. Also, gases (defined here as materials having a vapor pressure which exceeds the pressure within the bubbler at convenient bubbler temperatures) are not preferred for MOCVD because gases cannot be evaporated at a uniform rate in a bubbler. For example, arsine and phosphine have been supplied as gases in pressurized cylinders and metered directly into the deposition chamber.

Organometallic compounds for MOCVD desirably are liquids at bubbler pressure and at a temperature between about $-20°$ C. and about $40°$ C. Such compounds also should have a vapor pressure of at least about 1.0 torrs at the bubbler temperature, boil and decompose at temperatures substantially exceeding the bubbler temperature, and decompose readily at the temperature encountered in the deposition chamber.

Another problem facing practitioners of MOCVD is that arsine and phosphine, commonly employed as sources of arsenic- and phosphorus-containing deposition products, are highly toxic. They have been the subject of proposed and existing restrictive legislation. The triorganometallic compounds previously proposed to replace them, such as trimethylarsine, are far less toxic, but leave residual carbon decomposition products in the deposited films. (See Bhat, "OMCVD Growth of GaAs and AlGaAs Using a Solid as a Source", *Journal of Electronic Materials*, Vol. 14, No. 4, 1985, pp.433–449. Kuech, et al. "Reduction of Background Doping in Metal-Organic Vapor Phase Epitaxy of GaAs Using Triethyl Gallium at Low Reactor Pressures," *Appl.*

*Phys. Letters* I, Oct. 15, 1985, not believed to be prior art, also may have relevance because it discloses that gallium arsenide films made with trimethylgallium and arsine have more carbon residue than films made with triethylgallium.) Also, some triorganometallic compounds of arsenic and phosphorus may not have vapor pressures suitable for practicing MOCVD at a convenient temperature. Thus, new compounds which are effective replacements for arsine and phosphine, but less toxic, would be highly desirable.

The known organometallic compounds of elements in Groups 2B, 2A, 3A, 5A, or 6A of the Periodic Table, particularly bismuth, selenium, tellurium, beryllium, magnesium, or elements of Groups 2B or 3A of the Periodic Table, are relatively few in number. For example, the following compounds of these elements are all those lower alkyl, phenyl, alkyl-substituted phenyl, cyclopentadienyl, or alkyl-substituted cyclopentadienyl organometallic compounds listed in the *CRC Handbook of Chemistry and Physics*, 61st Edition, CRC Press, Inc., Boca Raton, Fla.:

ZINC
 Di-n-butylzinc
 Diethylzinc
 Dimethylzinc
 Diphenylzinc
 Di-n-propylzinc
 Di-o-tolylzinc
CADMIUM
 Dibutylcadmium
 Diethylcadmium
 Diisobutylcadmium
 Dimethylcadmium
 Dipropylcadmium
MERCURY
 Dibenzylmercury
 Di-n-butylmercury
 Diethylmercury
 Diisobutylmercury
 Diisopropylmercury
 Dimethylmercury
 Diphenylmercury
 Dipropylmercury
 Di-o-tolylmercury
 Di-m-tolylmercury
 Di-p-tolylmercury
BERYLLIUM
 Di-n-butylberyllium
 Diethylberyllium
 Dimethylberyllium
 Dipropylberyllium
MAGNESIUM
 Dimethylmagnesium
 Diphenylmagnesium
BORON
 Tribenzylboron
 Tri-n-butylboron
 Tri-t-butylboron
 Triethylboron
 Triisobutylboron
 Trimethylboron
 Triphenylboron
 Tri-n-propylboron
 Tri-sec-butylboron
 Tri-p-tolylboron
 Tri-p-xylylboron
ALUMINUM
 Diisobutylaluminum hydride
 Triethylaluminum
 Triisobutylaluminum
 Trimethylaluminum
 Triphenylaluminum
GALLIUM
 Triethylgallium
 Trimethylgallium
INDIUM
 Trimethylindium
 Triethylindium
THALLIUM
 Triethylthallium
 Trimethylthallium
PHOSPHORUS
 Trimethylphosphine
 Triethylphosphine
 Tripropylphosphine
 Tributylphosphine
 Triphenylphosphine
ARSENIC
 Dimethylarsine
 Methylarsine
 Phenylarsine
 Tribenzylarsine
 Trimethylarsine
 Triphenylarsine
ANTIMONY
 Pentamethylantimony
 Phenyldimethylantimony
 Tributylstibene
 Triethylantimony
 Trimethylantimony
 Triphenylantimony
BISMUTH
 Methylbismuthine
 Trimethylbismuthine
 Triethylbismuthine
 Triphenylbismuthine
 Tri-n-propylbismuth
SELENIUM
 Diethylselenide
TELLURIUM
 Dimethyltelluride
 Diethyltelluride Some additional compounds disclosed in the prior art include dicyclohexylphosphine (U.S. Pat. No. 3,547,881); various triorganophosphines (U.S. Ser. No. 691,598, filed Jan. 15, 1985); and the mono- and diorganic arsines and phosphines identified as prior art in Table II herein. See also Tzscach, et al., "Zur Synthese der Dialkylamine Dialkylarsine. Sowie der Dialkylarsine", *Zeitschrift fur Anorganische und Allegemaine Chemie*, Band 326, 1964 (pp. 280–287); and Horiguchu, et al., "Mass Spectrometric Study of Growth Reactions in Low Pressure CMVPE of GaAs by in situ Gas Sampling," presented at the 12th International Symposium on Gallium Arsenide and Related Compounds in Japan, 23–26 September, 1985 (this reference is not believed to be prior art).

Because there are few organometallic compounds of most of the listed elements, and particularly of aluminum, gallium, indium, selenium, tellurium, beryllium, and magnesium, there often will be no compound of a particular metal which is well suited to MOCVD. Furthermore, most of the previously listed compounds (with the exceptions of dimethylaluminum hydride, diethylaluminum hydride, diisobutylaluminum hydride, certain alkyl and dialkylarsines, phenylarsine, phenyldimethylantimony, and methylbismuthine) do not include more than one type of organic substituent on a given molecule. Particularly for Group 2B, 2A, and 3A elements of the Periodic Table it is difficult to select a useful candidate having the necessary properties for MOCVD.

Another factor complicates the selection of a workable organometallic compound for MOCVD: structurally related organometallic compounds often do not form homologous series. Many organometallic compounds characteristically exist in only one form, for example, as monomers, dimers, trimers, tetramers, or higher polymers. Structurally similar compounds often have different characteristic forms, and thus much different or inconsistent vapor pressures, melting points, and decomposition temperatures.

As a particular case in point, consider the two known compounds of indium—trimethylindium and triethylindium. Both of these compounds have been used to deposit indium containing films. (See: 1. Manasevit and Simpson, *J. Electrochem. Soc.*, 118, C291 (1971); 120, 135 (1973). 2. Bass, *J. Crystal Growth*, 31, 172 (1975). 3. Duchemin, et al., Paper 13, *7th Intern. Symp. on GaAs and Related Compounds*, Clayton, Md., September, 1978.) Though they are structurally similar, the respective melting points, vapor pressures at 30 degrees Celsius and decomposition temperatures of these compounds are inconsistent with what would be expected of homologs, as illustrated by Table I below:

TABLE I

| PROPERTY | TRIETHYLINDIUM | TRIMETHYLINDIUM |
|---|---|---|
| Melting Point | −32° C. | 88° C. |
| Vapor Pressure at 30° C. | 0.8 torrs | 7.2 torrs |
| Temperature of Onset of Decomposition | 40° C. | 150° C. |

Trimethylindium is known to characteristically form a tetramer in the solid form and triethylindium is believed to characteristically form a loose liquid polymer structure at room temperature. This difference is believed to underlie their inconsistent properties.

The preceding table illustrates that trimethylindium is a solid at temperatures employed in bubblers. Trimethylindium has been vaporized by providing two bubblers in series to better control the amount of entrained vapor. The apparatus necessary for this two bubbler procedure is more expensive and complex, and yet provides less control of the partial pressure of trimethylindium, than apparatus used to vaporize a liquid from a single bubbler. Triethylindium has an even lower vapor pressure at 30 degrees Celsius than trimethylindium, and is also less thermally and chemically stable than trimethylindium. Triethylindium starts to decompose to indium at 40 degrees Celsius, and at an even lower temperature in the presence of hydrogen—the typical carrier gas. The vaporization of triethylindium thus must take place at a temperature approaching its decomposition temperature, and even then the deposition rate is undesirably low. The lack of homology in these indium compounds and the small number of known indium compounds have prevented those of ordinary skill in the art from selecting an optimal compound for indium MOCVD.

SUMMARY OF THE INVENTION

A first aspect of the invention is a genus of compounds useful for metal organic chemical vapor deposition, comprising all the novel compounds defined by the molecular formula:

wherein N is either phosphorus or arsenic, H is hydride, and X or Y are selected from hydrocarbons or hydride (but are not both hydride). These novel compounds are less toxic than the corresponding trihydride, but can scavenge hydrocarbons from the deposition chamber (unlike the corresponding triorganic substituted arsine or phosphine). Most are in a convenient physical form (liquid and stable at some temperature between 0° C. and 150° C. and a pressure not greater than about one atmosphere) for being supplied from bubblers. Three additional advantages of many of these compounds are that they are either nonpyrophoric or less pyrophoric than the corresponding trihydrides; the pure liquids can be stored under subatmospheric pressure and thus are not as prone to escaping as arsine or phosphine gases (which are stored under pressure greater than atmospheric pressure); and they decompose at comparable or lower temperatures than arsine or phosphine, so a lower deposition temperature and other comparable or milder deposition conditions can be successfully used.

A second aspect of the invention is a chemical vapor deposition process in which compounds according to the previous paragraph, or known mono- or diorganic arsine or phosphine derivatives, are used as source materials.

A third aspect of the invention is a metal organic chemical vapor deposition process comprising three steps. As the first step, first and second compounds are selected, each having the formula:

wherein x is an integer from 2 to 4 inclusive; each said R substituent is independently selected from hydride, lower alkyl, phenyl, alkyl-substituted phenyl, cyclopentadienyl, and alkyl-substituted cyclopentadienyl; and M is selected from elements of Groups 2B, 2A, 3A, 5A and 6A of the Periodic Table, except for carbon, nitrogen, oxygen, and sulfur. The respective R substituents of the first and second compounds are different, and preferably mutually exclusive. All the R groups of the first compound can be the same, and all the R groups of the second compound can be the same. As the second step, a composite compound is made by any process. The composite compound also has the formula $MR_x$, is different than the first and second compounds, and has at least one R substituent possessed by the first compound and at least one different R substituent possessed by the second compound. The composite compound differs from the first and second compounds as to at least one property selected from decomposition temperature, vapor pressure, and melting point. As the third and final step, the composite compound is employed for metal organic chemical vapor deposition in apparatus comprising a deposition chamber maintained at a temperature, between the melting point and decomposition temperature of the composite compound, at which the composite compound has a vapor pressure which is useful for a particular deposition process. The apparatus further comprises a deposition chamber maintained at a temperature at least as high as the decomposition temperature of the composite compound. Practice of this process allows one to tailor the molecular structure of an organometallic compound of a desired metal to fit the required specifications of vapor pressure, melting point, boiling point and decomposition temperature which are necessary for successful or optimal practice of MOCVD.

DESCRIPTION OF PREFERRED EMBODIMENTS

Figure 1:
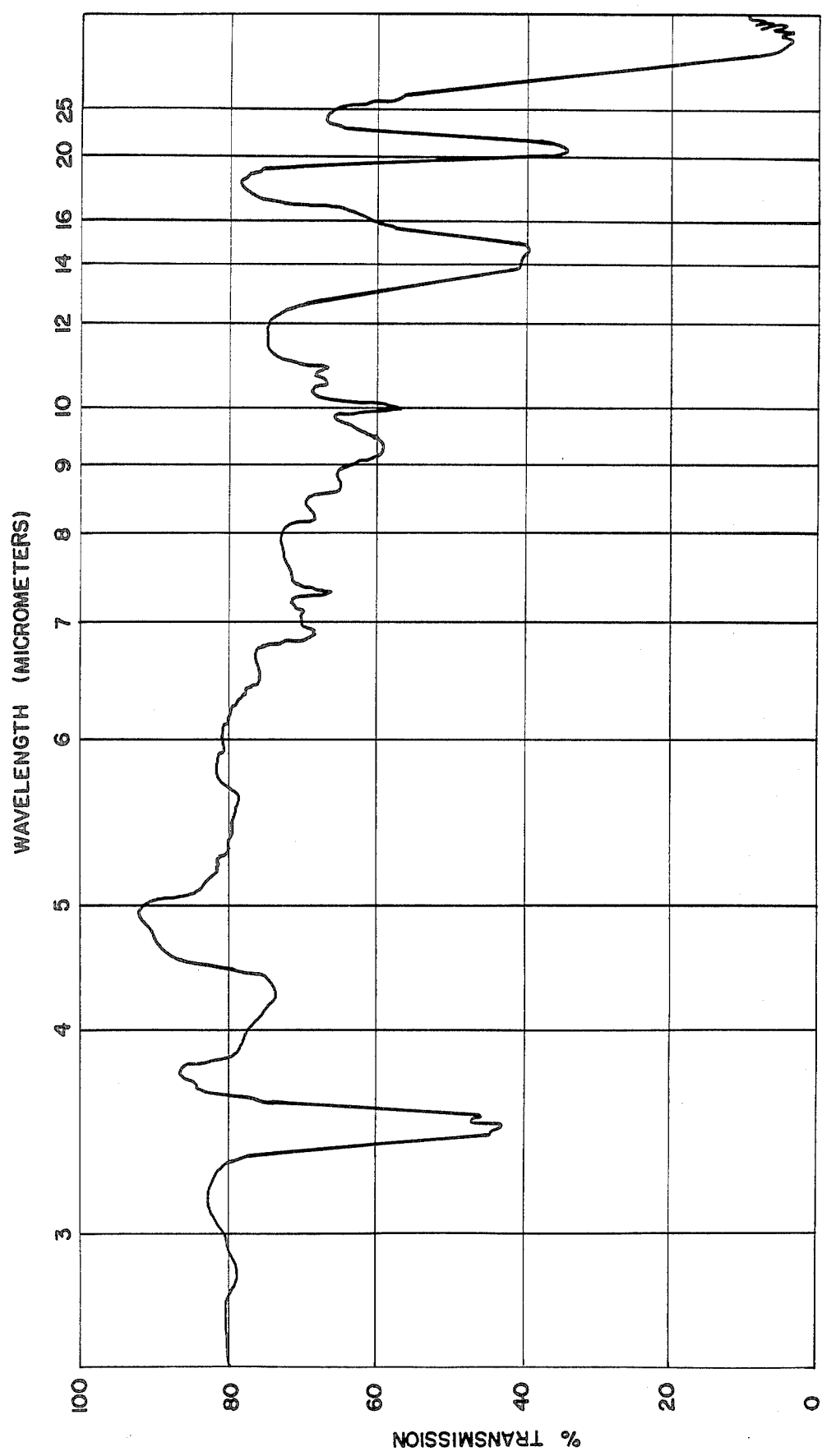
FIG. 1 is an infrared absorption spectrum of dimethylethylindium.

The novel arsenic and phosphorus compounds of the present invention have the formula:

wherein N is arsenic or phosphorus; H is hydride; X and Y are selected from alkyl having from 1 to 5 carbon atoms, aryl, and cycloalkyl; but not both X and Y are hydride and previously known compounds are excluded. These compounds are exemplified by Table II, listing all arsenic and phosphorus compounds in which X and Y are independently selected from hydride, alkyl having from 1 to 5 carbon atoms, cyclopentadienyl, and phenyl.

TABLE II

| Species | N | X | Y |
|---|---|---|---|
| 1* | arsenic | hydride | hydride |
| 2* | arsenic | hydride | methyl |
| 3* | arsenic | hydride | ethyl |
| 4* | arsenic | hydride | n-propyl |
| 5* | arsenic | hydride | i-propyl |
| 6* | arsenic | hydride | n-butyl |
| 7 | arsenic | hydride | s-butyl |
| 8 | arsenic | hydride | i-butyl |
| 9* | arsenic | hydride | t-butyl |
| 10 | arsenic | hydride | n-pentyl |
| 11 | arsenic | hydride | i-pentyl |
| 12 | arsenic | hydride | t-pentyl |
| 13 | arsenic | hydride | neopentyl |
| 14 | arsenic | hydride | cyclopentadienyl |
| 15* | arsenic | hydride | phenyl |
| 16* | arsenic | methyl | methyl |
| 17* | arsenic | methyl | ethyl |
| 18* | arsenic | methyl | n-propyl |
| 19 | arsenic | methyl | i-propyl |
| 20 | arsenic | methyl | n-butyl |
| 21 | arsenic | methyl | s-butyl |
| 22 | arsenic | methyl | i-butyl |
| 23 | arsenic | methyl | t-butyl |
| 24 | arsenic | methyl | n-pentyl |
| 25 | arsenic | methyl | i-pentyl |
| 26 | arsenic | methyl | t-pentyl |
| 27 | arsenic | methyl | neopentyl |
| 28 | arsenic | methyl | cyclopentadienyl |
| 29* | arsenic | methyl | phenyl |
| 30* | arsenic | ethyl | ethyl |
| 31 | arsenic | ethyl | n-propyl |
| 32 | arsenic | ethyl | i-propyl |
| 33 | arsenic | ethyl | n-butyl |
| 34 | arsenic | ethyl | s-butyl |
| 35 | arsenic | ethyl | i-butyl |
| 36 | arsenic | ethyl | t-butyl |
| 37 | arsenic | ethyl | n-pentyl |
| 38 | arsenic | ethyl | i-pentyl |
| 39 | arsenic | ethyl | t-pentyl |
| 40 | arsenic | ethyl | neopentyl |
| 41 | arsenic | ethyl | cyclopentadienyl |
| 42 | arsenic | ethyl | phenyl |
| 43* | arsenic | n-propyl | n-propyl |
| 44 | arsenic | n-propyl | i-propyl |
| 45 | arsenic | n-propyl | n-butyl |
| 46 | arsenic | n-propyl | s-butyl |
| 47 | arsenic | n-propyl | i-butyl |
| 48 | arsenic | n-propyl | t-butyl |
| 49 | arsenic | n-propyl | n-pentyl |
| 50 | arsenic | n-propyl | i-pentyl |
| 51 | arsenic | n-propyl | t-pentyl |
| 52 | arsenic | n-propyl | neopentyl |
| 53 | arsenic | n-propyl | cyclopentadienyl |
| 54 | arsenic | n-propyl | phenyl |
| 55* | arsenic | i-propyl | i-propyl |
| 56 | arsenic | i-propyl | n-butyl |
| 57 | arsenic | i-propyl | s-butyl |
| 58 | arsenic | i-propyl | i-butyl |
| 59 | arsenic | i-propyl | t-butyl |
| 60 | arsenic | i-propyl | n-pentyl |
| 61 | arsenic | i-propyl | i-pentyl |
| 62 | arsenic | i-propyl | t-pentyl |
| 63 | arsenic | i-propyl | neopentyl |
| 64 | arsenic | i-propyl | cyclopentadienyl |
| 65 | arsenic | i-propyl | phenyl |
| 66* | arsenic | n-butyl | n-butyl |
| 67 | arsenic | n-butyl | s-butyl |
| 68 | arsenic | n-butyl | i-butyl |
| 69 | arsenic | n-butyl | t-butyl |
| 70 | arsenic | n-butyl | n-pentyl |
| 71 | arsenic | n-butyl | i-pentyl |
| 72 | arsenic | n-butyl | t-pentyl |
| 73 | arsenic | n-butyl | neopentyl |
| 74 | arsenic | n-butyl | cyclopentadienyl |
| 75 | arsenic | n-butyl | phenyl |
| 76 | arsenic | s-butyl | s-butyl |
| 77 | arsenic | s-butyl | i-butyl |
| 78 | arsenic | s-butyl | t-butyl |
| 79 | arsenic | s-butyl | n-pentyl |
| 80 | arsenic | s-butyl | i-pentyl |
| 81 | arsenic | s-butyl | t-pentyl |
| 82 | arsenic | s-butyl | neopentyl |
| 83 | arsenic | s-butyl | cyclopentadienyl |
| 84 | arsenic | s-butyl | phenyl |
| 85 | arsenic | i-butyl | i-butyl |
| 86 | arsenic | i-butyl | t-butyl |
| 87 | arsenic | i-butyl | n-pentyl |
| 88 | arsenic | i-butyl | i-pentyl |
| 89 | arsenic | i-butyl | t-pentyl |
| 90 | arsenic | i-butyl | neopentyl |
| 91 | arsenic | i-butyl | cyclopentadienyl |
| 92 | arsenic | i-butyl | phenyl |
| 93 | arsenic | t-butyl | t-butyl |
| 94 | arsenic | t-butyl | n-pentyl |
| 95 | arsenic | t-butyl | i-pentyl |
| 96 | arsenic | t-butyl | t-pentyl |
| 97 | arsenic | t-butyl | neopentyl |
| 98 | arsenic | t-butyl | cyclopentadienyl |
| 99 | arsenic | t-butyl | phenyl |
| 100 | arsenic | n-pentyl | n-pentyl |
| 101 | arsenic | n-pentyl | i-pentyl |
| 102 | arsenic | n-pentyl | t-pentyl |
| 103 | arsenic | n-pentyl | neopentyl |
| 104 | arsenic | n-pentyl | cyclopentadienyl |
| 105 | arsenic | n-pentyl | phenyl |
| 106 | arsenic | i-pentyl | i-pentyl |
| 107 | arsenic | i-pentyl | t-pentyl |

TABLE II-continued

| Species | N | X | Y |
|---|---|---|---|
| 108 | arsenic | i-pentyl | neopentyl |
| 109 | arsenic | i-pentyl | cyclopentadienyl |
| 110 | arsenic | i-pentyl | phenyl |
| 111 | arsenic | t-pentyl | t-pentyl |
| 112 | arsenic | t-pentyl | neopentyl |
| 113 | arsenic | t-pentyl | cyclopentadienyl |
| 114 | arsenic | t-pentyl | phenyl |
| 115 | arsenic | neopentyl | neopentyl |
| 116 | arsenic | neopentyl | cyclopentadienyl |
| 117 | arsenic | neopentyl | phenyl |
| 118 | arsenic | cyclopentadienyl | cyclopentadienyl |
| 119 | arsenic | cyclopentadienyl | phenyl |
| 120* | arsenic | phenyl | phenyl |
| 121* | phosphorus | hydride | hydride |
| 122* | phosphorus | hydride | methyl |
| 123* | phosphorus | hydride | ethyl |
| 124* | phosphorus | hydride | n-propyl |
| 125* | phosphorus | hydride | i-propyl |
| 126* | phosphorus | hydride | n-butyl |
| 127 | phosphorus | hydride | s-butyl |
| 128* | phosphorus | hydride | i-butyl |
| 129* | phosphorus | hydride | t-butyl |
| 130* | phosphorus | hydride | n-pentyl |
| 131 | phosphorus | hydride | i-pentyl |
| 132 | phosphorus | hydride | t-pentyl |
| 133 | phosphorus | hydride | neopentyl |
| 134 | phosphorus | hydride | cyclopentadienyl |
| 135* | phosphorus | hydride | phenyl |
| 136* | phosphorus | methyl | methyl |
| 137* | phosphorus | methyl | ethyl |
| 138* | phosphorus | methyl | n-propyl |
| 139 | phosphorus | methyl | i-propyl |
| 140* | phosphorus | methyl | n-butyl |
| 141 | phosphorus | methyl | s-butyl |
| 142 | phosphorus | methyl | i-butyl |
| 143 | phosphorus | methyl | t-butyl |
| 144 | phosphorus | methyl | n-pentyl |
| 145 | phosphorus | methyl | i-pentyl |
| 146 | phosphorus | methyl | t-pentyl |
| 147 | phosphorus | methyl | neopentyl |
| 148 | phosphorus | methyl | cyclopentadienyl |
| 149 | phosphorus | methyl | phenyl |
| 150* | phosphorus | ethyl | ethyl |
| 151 | phosphorus | ethyl | n-propyl |
| 152 | phosphorus | ethyl | i-propyl |
| 153 | phosphorus | ethyl | n-butyl |
| 154 | phosphorus | ethyl | s-butyl |
| 155 | phosphorus | ethyl | i-butyl |
| 156 | phosphorus | ethyl | t-butyl |
| 157 | phosphorus | ethyl | n-pentyl |
| 158 | phosphorus | ethyl | i-pentyl |
| 159 | phosphorus | ethyl | t-pentyl |
| 160 | phosphorus | ethyl | neopentyl |
| 161 | phosphorus | ethyl | cyclopentadienyl |
| 162 | phosphorus | ethyl | phenyl |
| 163 | phosphorus | n-propyl | n-propyl |
| 164 | phosphorus | n-propyl | i-propyl |
| 165 | phosphorus | n-propyl | n-butyl |
| 166 | phosphorus | n-propyl | s-butyl |
| 167 | phosphorus | n-propyl | i-butyl |
| 168 | phosphorus | n-propyl | t-butyl |
| 169 | phosphorus | n-propyl | n-pentyl |
| 170 | phosphorus | n-propyl | i-pentyl |
| 171 | phosphorus | n-propyl | t-pentyl |
| 172 | phosphorus | n-propyl | neopentyl |
| 173 | phosphorus | n-propyl | cyclopentadienyl |
| 174 | phosphorus | n-propyl | phenyl |
| 175 | phosphorus | i-propyl | i-propyl |
| 176 | phosphorus | i-propyl | n-butyl |
| 177 | phosphorus | i-propyl | s-butyl |
| 178 | phosphorus | i-propyl | i-butyl |
| 179 | phosphorus | i-propyl | t-butyl |
| 180 | phosphorus | i-propyl | n-pentyl |
| 181 | phosphorus | i-propyl | i-pentyl |
| 182 | phosphorus | i-propyl | t-pentyl |
| 183 | phosphorus | i-propyl | neopentyl |
| 184 | phosphorus | i-propyl | cyclopentadienyl |
| 185 | phosphorus | i-propyl | phenyl |
| 186* | phosphorus | n-butyl | n-butyl |
| 187 | phosphorus | n-butyl | s-butyl |
| 188 | phosphorus | n-butyl | i-butyl |
| 189 | phosphorus | n-butyl | t-butyl |
| 190 | phosphorus | n-butyl | n-pentyl |
| 191 | phosphorus | n-butyl | i-pentyl |
| 192 | phosphorus | n-butyl | t-pentyl |
| 193 | phosphorus | n-butyl | neopentyl |
| 194 | phosphorus | n-butyl | cyclopentadienyl |
| 195 | phosphorus | n-butyl | phenyl |
| 196 | phosphorus | s-butyl | s-butyl |
| 197 | phosphorus | s-butyl | i-butyl |
| 198 | phosphorus | s-butyl | t-butyl |
| 199 | phosphorus | s-butyl | n-pentyl |
| 200 | phosphorus | s-butyl | i-pentyl |
| 201 | phosphorus | s-butyl | t-pentyl |
| 202 | phosphorus | s-butyl | neopentyl |
| 203 | phosphorus | s-butyl | cyclopentadienyl |
| 204 | phosphorus | s-butyl | phenyl |
| 205 | phosphorus | i-butyl | i-butyl |
| 206 | phosphorus | i-butyl | t-butyl |
| 207 | phosphorus | i-butyl | n-pentyl |
| 208 | phosphorus | i-butyl | i-pentyl |
| 209 | phosphorus | i-butyl | t-pentyl |
| 210 | phosphorus | i-butyl | neopentyl |
| 211 | phosphorus | i-butyl | cyclopentadienyl |
| 212 | phosphorus | i-butyl | phenyl |
| 213* | phosphorus | t-butyl | t-butyl |
| 214 | phosphorus | t-butyl | n-pentyl |
| 215 | phosphorus | t-butyl | i-pentyl |
| 216 | phosphorus | t-butyl | t-pentyl |
| 217 | phosphorus | t-butyl | neopentyl |
| 218 | phosphorus | t-butyl | cyclopentadienyl |
| 219 | phosphorus | t-butyl | phenyl |
| 220 | phosphorus | n-pentyl | n-pentyl |
| 221 | phosphorus | n-pentyl | i-pentyl |
| 222 | phosphorus | n-pentyl | t-pentyl |
| 223 | phosphorus | n-pentyl | neopentyl |
| 224 | phosphorus | n-pentyl | cyclopentadienyl |
| 225 | phosphorus | n-pentyl | phenyl |
| 226 | phosphorus | i-pentyl | i-pentyl |
| 227 | phosphorus | i-pentyl | t-pentyl |
| 228 | phosphorus | i-pentyl | neopentyl |
| 229 | phosphorus | i-pentyl | cyclopentadienyl |
| 230 | phosphorus | i-pentyl | phenyl |
| 231 | phosphorus | t-pentyl | t-pentyl |
| 232 | phosphorus | t-pentyl | neopentyl |
| 233 | phosphorus | t-pentyl | cyclopentadienyl |
| 234 | phosphorus | t-pentyl | phenyl |
| 235 | phosphorus | neopentyl | neopentyl |
| 236 | phosphorus | neopentyl | cyclopentadienyl |
| 237 | phosphorus | neopentyl | phenyl |
| 238 | phosphorus | cyclopentadienyl | cyclopentadienyl |
| 239 | phosphorus | cyclopentadienyl | phenyl |
| 240* | phosphorus | phenyl | phenyl |

35 of the 240 compounds named in the Table II (species 1–6, 9, 15–18, 29, 30, 43, 55, 66, 120–126, 128, 129, 130, 135, 136, 137, 138, 140, 150, 186, 213, and 240) are not novel, but the remaining species are. (Hereinafter, if no particular isomer of an alkyl group is specified, any isomer is intended.)

The preparation of the arsenic compounds is exemplified in Example 1 and by Doak, et al., *Organometallic Compounds of Arsenic, Antimony, and Bismuth* (New York: Wiley-Interscience), pp 120–127; and Hagihara, et al., *Handbook of Organometallic Compounds* (New York: W. A. Benjamin, Inc.) 1968, pp. 720–726.

The preparation of the phosphorus compounds is exemplified by diethylphosphine, prepared as follows:

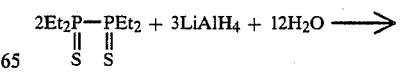

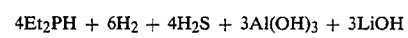

(Literature reference: *Inorganic Chemistry* 1962, 1(3), 471.) Other substituted phosphines can be prepared by substituting X and Y moieties from Table II for the two ethyl groups attached to phosphorus in the starting material used in the above reaction. Preparations for certain organophosphines found useful herein, but not their utility, are also disclosed in Hagihara, et al., *Handbook of Organometallic Compounds* (New York: W. A. Benjamin, Inc.), 1968, pp. 560, 566, 571, 574, 579, and 580; and Kosolapoff, et al., *Organic Phosphorus Compounds*, Vol. 1 (New York: Wiley-Interscience), pp. 4–11 and 16–27.

Hybrid organic analogs of arsine and phosphine (in which X and Y are different) also can be produced by mixing two analogs, each one including one of the respective substituents of the hybrid; by reacting a halogen substituted organometallic compound with an alkylating or arylating agent to add an unlike substituent; by reacting the metal for which an organometallic hybrid compound is desired with mixtures of organic halides; by substituting a more active metal for a less active metal in an organometallic hybrid compound of the less active metal; or by other means. These reactions are similar to the methods set forth later for preparing hybrid organometallic compounds.

As indicated previously, the above novel compounds, as well as known species in Table II, have utility as reactants in MOCVD. Preferred reactants for this utility have a melting point of less than about 30 degrees Celsius, have a vapor pressure of at least 1.0 torr at a temperature within the bubbler temperature range of from about minus 20 degrees Celsius to about 40 degrees Celsius, are stable at the indicated bubbler temperatures but readily decompose at a deposition chamber temperature of from about 200 to about 800 degrees Celsius, preferably from about 550 to about 700 degrees Celsius, and are inert at bubbler temperatures with respect to at least one carrier gas such as hydrogen, nitrogen, or helium.

The present compounds also have utility for the preparation of other such compounds within the scope of the present invention. For example, a listed compound which does not have a desirable decomposition temperature may be reacted with another organometallic compound to produce a new hybrid.

The ultimate utility of these compounds, employed in MOCVD, is to provide dopants or coatings of the arsenic or phosphorus oxides, nitrides, III-V compounds, and so forth.

PROCESS FOR SELECTING AND USING HYBRID ORGANOMETALLIC COMPOUNDS FOR MOCVD

A third aspect of the present invention is a process for selecting particular hybrid organometallic compounds of Group 2B, 2A, 3A, 5A, and 6A elements which are useful in metal organic chemical vapor deposition processes.

The present process, characterized as an MOCVD process, comprises the steps of selecting first and second compounds, each having the formula $MR_x$ as further defined below, making a hybrid compound having at least one substituent in common with the first compound and at least one substituent in common with the second compound, and employing the hybrid compound for metal organic chemical vapor deposition in apparatus further specified below.

Looking more closely at the step of selecting first and second compounds, the compounds from which the selection is made have the formula $MR_x$ The M substituents are selected from elements of Groups 2B, 2A, 3A, 5A, and 6A of the Periodic Table, except for Carbon, Nitrogen, Oxygen, and Sulfur. Since in the usual chemical vapor deposition process a particular element has been selected for deposition, usually the M constituents of the first and second compounds will be the same. However, the process is not limited by this consideration. R substituents contemplated for use in the novel compounds include hydride, lower alkyl, phenyl, alkyl-substituted phenyl, cyclopentadienyl, and alkyl-substituted cyclopentadienyl. Lower alkyl is defined herein as a substituent having from one to four carbon atoms, and specifically includes methyl, ethyl, n-propyl, isopropyl, n-butyl, s-butyl, isobutyl, and t-butyl. Alkyl-substituted phenyl as defined herein includes alkyl-substituted phenyl and phenyl-substituted alkyl, alkyl being lower alkyl as exemplified above. Specific substituents contemplated within the meaning of alkyl-substituted phenyl are as follows: benzyl; tolyl in ortho, meta, or para positions with respect to the metal; xylyl, including orientations in which the methyl substituents are ortho with respect to each other and respectively ortho and meta or meta and para with respect to the metal, or if the methyl substituents are meta, situations in which the methyl substituents are respectively ortho and ortho, or ortho and para, or meta and meta with respect to the metal atom, and if the methyl substituents are para, the situation in which the methyl substituents are ortho and meta to the metal substituent of the phenyl; ethylphenyl, isopropylphenyl, butylphenyl, isobutylphenyl, t-butylphenyl, these substituents being in ortho, meta, or para relation to the metal atom; and any other phenyl having one or more of the alkyl substituents previously defined. Alkyl-substituted cyclopentadienyl as defined herein includes alkyl-substituted cyclopentadienyl and cyclopentadienyl substituted alkyl, alkyl being lower alkyl as exemplified above. Specific substituents contemplated within the meaning of alkyl-substituted cyclopentadienyl are as follows: methylcyclopentadienyl, 4-(cyclopentadienyl)-n-butyl, pentamethylcyclopentadienyl, and cyclopentadienyl substituted by up to six like or different lower alkyl groups and linked directly or by one of the lower alkyl groups to the selected metal atom. All R substituents on the first compound can be alike or different, as can all R substituents on the second compound. "x" is an integer from 2 to 4 inclusive, depending upon the valence of the chosen metal. The process is particularly useful when neither the first compound nor the second compound has an optimal melting point, vapor pressure, or decomposition temperature for use in MOCVD. First and second compounds meeting this definition are trimethylindium and triethylindium, whose melting points, volatility, and decomposition temperatures are set forth above in Table I.

Other examples of first and second compounds useful in practicing the present invention can be found in the list of known homosubstituted and hybrid organometallic compounds in the "BACKGROUND ART" section set forth previously; and in the species list in the description of arsenic and phosphorus compounds.

Once first and second compounds have been selected, the next step is to make a composite compound having at least one R substituent possessed by the first compound and at least one different R substituent possessed by the second compound. Although one manner of synthesizing the composite compound is by mixing the first and second compounds, the present process is not limited to a particular method of synthesis. The other synthetic methods described below, or methods not specifically disclosed herein, can also be used within the scope of the present process invention. To practice the mixing method described in the preceding paragraph, the first and second compounds are mixed together and allowed to equilibrate at a temperature below the lower of the boiling points of the reactants and products, preferably from 0°–30° Celsius. A nonreactive solvent such as benzene, hexane, ether, tetrahydrofuran, etc. is optional. The result of this exchange reaction will typically be a major proportion of a hybrid organometallic compound according to the invention, in which the several R substituents are present in roughly the same proportions as in the reaction mixture containing the first and second reactants. Minor proportions of the reactants and of other organometallic products may also be present. The desired product can be isolated by distillation, crystallization, or other well known processes. Alternatively, the product mixture can be used for MOCVD without isolating a pure hybrid product. The following equations illustrate reactions of this type in which stoichiometric proportions of the reactants provide a major proportion of the indicated product:

$$2(CH_3)_3In(s) + (C_2H_5)_3In(l) \rightarrow 3(CH_3)_2C_2H_5In(l)$$

$$2(C_2H_5)_3In(l) + (CH_3)_3In(s) \rightarrow 3(C_2H_5)_2CH_3In(l)$$

In a second synthetic method, a halogenated organometallic compound having one of the desired alkyl, phenyl, alkyl-substituted phenyl, cyclopentadienyl, or alkyl-substituted cyclopentadienyl substituents is reacted with an alkylating or arylating agent. The alkyl or aryl group of the alkylating or arylating agent then replaces the halogen substituent of the organometallic compound. Typical alkylating agents for use herein include such materials as methyllithium, ethylmagnesium bromide, or lithium aluminum hydride. Examples of these synthetic reactions are set forth in the three following equations:

$$(C_2H_5)_2InCl + CH_3Li \rightarrow CH_3(C_2H_5)_2In + LiCl$$

$$CH_3ZnBr + C_2H_5MgBr \rightarrow CH_3C_2H_5Zn + MgBr_2$$

$$(CH_3)_3Al + LiAlH_4 \rightarrow (CH_3)_2AlH + LiAlH_3(CH_3)$$

The reaction of metals with mixtures of organic halides to produce hybrid organometallic compounds is useful, and is illustrated by the following reaction:

$$CH_3Br + C_2H_5Br + 2Se \rightarrow CH_3C_2H_5Se + SeBr_2$$

A metal displacement reaction can be used, and is exemplified by the following reaction:

$$2Ga + 3Hg(CH_3)_2 \rightarrow 2Ga(CH_3)_3 + 3Hg$$

In the above reaction, it will be appreciated that the metal of the organometallic reactant must be a less active metal than the substituting metal.

Other methods ordinarily used in organometallic synthesis, such as those discussed on pages 345–348 and 365–366 of Roberts and Caserio, *Basic Principles of Organic Chemistry*, W. A Benjamin Inc. (New York: 1964) can also be adapted to synthesize the hybrid organometallic compounds defined herein.

The composite compound, however made, should differ from each of the first and second compounds as to at least one property selected from decomposition temperature, vapor pressure at a particular temperature suitable for a bubbler, and melting point. By differing in respect to at least one of these properties, the composite compound will be useful for MOCVD under different process conditions than the first and second compounds. When one of the first and second compounds has a property such as melting point which is too low for a conventional MOCVD process and the other compound has a corresponding property which is too high for MOCVD, the composite compound defined herein may have a corresponding property between those of the first and second compounds or may have a surprisingly different value of the corresponding property.

Examples of the composite compounds within the scope of the second step of the process include the generic class and species set forth previously for the compound invention, as well as the previously mentioned hybrid organometallic compounds known to the art. Still further examples of such compounds are the following:
dimethylethylantimony
dimethylbutylphosphine
dimethylphenylarsine The above species can be made in the same manner as other hybrid organometallic compounds disclosed herein, such as by respectively mixing and equilibrating trimethylantimony and triethylantimony; trimethylphosphine and tributylphosphine; and trimethylarsine and triphenylarsine.

As a final step, the composite compound is employed for MOCVD in apparatus comprising a bubbler or equivalent apparatus maintained at a temperature between the melting point and decomposition temperature of the composite compound. The desired composite compound will have a vapor pressure at this temperature of at least 1.0 torrs, and thus will be useful for deposition. The MOCVD apparatus used in this step further comprises a deposition chamber maintained at a temperature at least as high as the decomposition temperature of the composite compound, triggering the breakdown of the composite organometallic compound to release its constituent metal.

The present hybrid organometallic compounds have an advantage over any nonazeotropic mixture for use in MOCVD, as any nonazeotropic mixture will be fractionated by the carrier gas in a manner analogous to gas liquid chromatography.

In the above process invention, the preferred compounds are selected from:
methylethylzinc;
methylbenzyltelluride;
dimethylethylboron;
dimethylethylthallium;
methylxylylselenium;
methylphenylgallium hydride;
ditolylgallium hydride;
and compounds having the formula:

$$MR_x$$

wherein X is an integer from 2 to 4 inclusive, each said R substituent is independently selected from hydride, lower alkyl, phenyl, alkyl-substituted phenyl, cyclopentadienyl, and alkyl-substituted cyclopentadienyl, at least two of said R substituents are different, and M is an element selected from cadmium, aluminum, gallium, indium, and bismuth, but excluding aluminum, bismuth, and gallium if any R is hydride. The selected compound is placed in a bubbler and used as a source of metal constituent M in a chemical vapor deposition process.

EXAMPLES

The following examples are provided to further exemplify the present compound and process inventions. The examples do not limit the scope of the invention, which is defined by the claims found at the end of the specification. All manipulations described are performed under a purified nitrogen atmosphere or under vacuum, unless the contrary is stated.

EXAMPLE 1

SYNTHESIS OF DIETHYLARSINE

First, diethylaminodichlorarsine is synthesized. A three-neck, one liter flask is equipped with a mechanical stirrer, condenser and dropping funnel, and charged with 164 g. (0.905 mol) of arsenic trichloride. The arsenic trichloride is dissolved in 300 ml of diethyl ether. Diethylamine (132 g., 1.81 mol) is added to the flask (through the dropping funnel), and the contents of the flask are stirred for two hours at room temperature. The contents are then filtered to remove the diethylamine hydrochloride byproduct. The filtrate is used directly in the next reaction.

Next, diethylaminodiethylarsine is prepared. A similarly equipped three-neck, two liter flask is arranged so the dropping funnel aims into the flask, rather than dropping its contents down the wall of the flask. The flask is charged with the filtrate from the previous reaction (diethylaminodichlorarsine and diethyl ether). Two moles of ethylmagnesium bromide (3 molar solution in diethyl ether) are added dropwise to the reaction flask through the dropping funnel and the contents are stirred overnight at room temperature. The reaction mixture is filtered and the filter cake is washed with diethyl ether. The filtrate is used directly in the next reaction.

Third, diethylchloroarsine is prepared. A three-neck, two liter flask is equipped with a fritted gas inlet tube, mechanical stirrer, and condenser and charged with the filtrate from the previous reaction (diethylaminodiethylarsine and diethyl ether). Hydrogen chloride gas is bubbled through the solution with stirring at room temperature until a precipitate forms and then redissolves (10–30 minutes). Excess HCl is distilled out of the two liter flask along with diethyl ether at atmospheric pressure. A precipitate of diethylamine hydrochloride reappears. The mixture is filtered to remove the by-product, diethylamine hydrochloride. The filtrate (diethylchloroarsine and diethyl ether) is used directly in the next reaction.

Fourth, diethylarsine is prepared. The filtrate from the previous reaction (diethylchloroarsine and diethyl ether, total weight 98 g) is transferred under a nitrogen atmosphere into a 250 ml dropping funnel. A three-neck, one liter flask is equipped with a magnetic stirrer, condenser, and the dropping funnel containing the filtrate from the previous reaction. The flask is charged with 5 grams (0.13 mol) of lithium aluminum hydride and 200 ml. of diethyl ether. The contents of the dropping funnel are then added slowly to the reaction flask while the contents are stirred vigorously. After the dropping funnel has been emptied, it is charged with 20 ml. of degassed water. The water is then added slowly with stirring to the reaction mixture. The contents of the three-neck reaction flask are transferred under a nitrogen atmosphere to a one liter separatory funnel and the aqueous layer is removed and discarded. The ether layer is transferred into a 500 ml. flask containing 200 g of anhydrous sodium sulfate and the mixture is stirred overnight and then filtered. Diethyl ether is removed from the filtrate by distillation at atmospheric pressure. The final product, diethylarsine, is isolated by atmospheric pressure distillation at 100°–110° C. as a clear, colorless liquid (46 g, 38% overall yield based on arsenic trichloride).

The other di-substituted arsines of Table II are synthesized by substituting for the two moles of ethylmagnesium bromide one mole of an alkylmagnesium bromide in which the alkyl group is the X substituent in Table II, and one mole of an alkylmagnesium bromide in which the alkyl group is the Y substituent in Table II.

EXAMPLE 2

Figure 2:
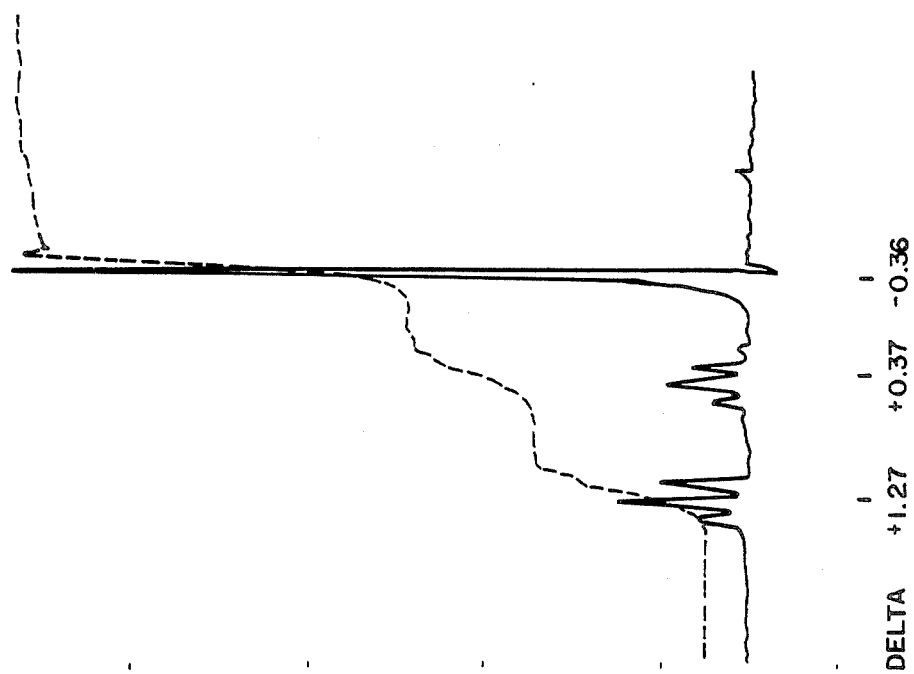
FIG. 2 is a proton nuclear magnetic resonance spectrum of dimethylethylindium.

SYNTHESIS OF DIMETHYLETHYLINDIUM 3.00 ml. of triethylindium (3.78 g., 0.0187 mol) was added to 5.988 g. (0.0374 mol) of trimethylindium in a 50 ml. flask in a glove bag under an argon atmosphere. The reagents were stirred at room temperature overnight. Reaction was essentially complete when all of the trimethylindium was fully reacted, leaving no residual solids. The resulting clear liquid was then distilled under full vacuum (about 1.5 torrs pressure). Some of the resulting dimethylethylindium distilled over at room temperature, or about 23 degrees Celsius. Gentle heating caused the rest to come over at 25 degrees Celsius, this temperature being measured at the distillation head. The resulting product had a melting point of about 5 to 7 degrees Celsius and a boiling point of 23°–25° C. at 1.5 torrs, which is unexpectedly different than the respective melting points and boiling points of trimethylindium and triethylindium. Proton nuclear magnetic resonance and infrared spectra were taken, and are presented as FIGS. 1 and 2 forming a part of this specification. For comparison, the NMR spectra of trimethylindium and triethylindium are presented as FIGS. 5 and 6. The infrared spectrum is not believed to distinguish the product compound, but the NMR spectrum of dimethylethylindium is characterized by peaks at delta +1.27 (triplet representing ethyl); +0.37 (quartet representing ethyl); and −0.36 (singlet representing methyl). Integration of the areas under the peaks provides the ratio of methyl to ethyl groups, which is 2:1.

EXAMPLE 3

Figure 4:
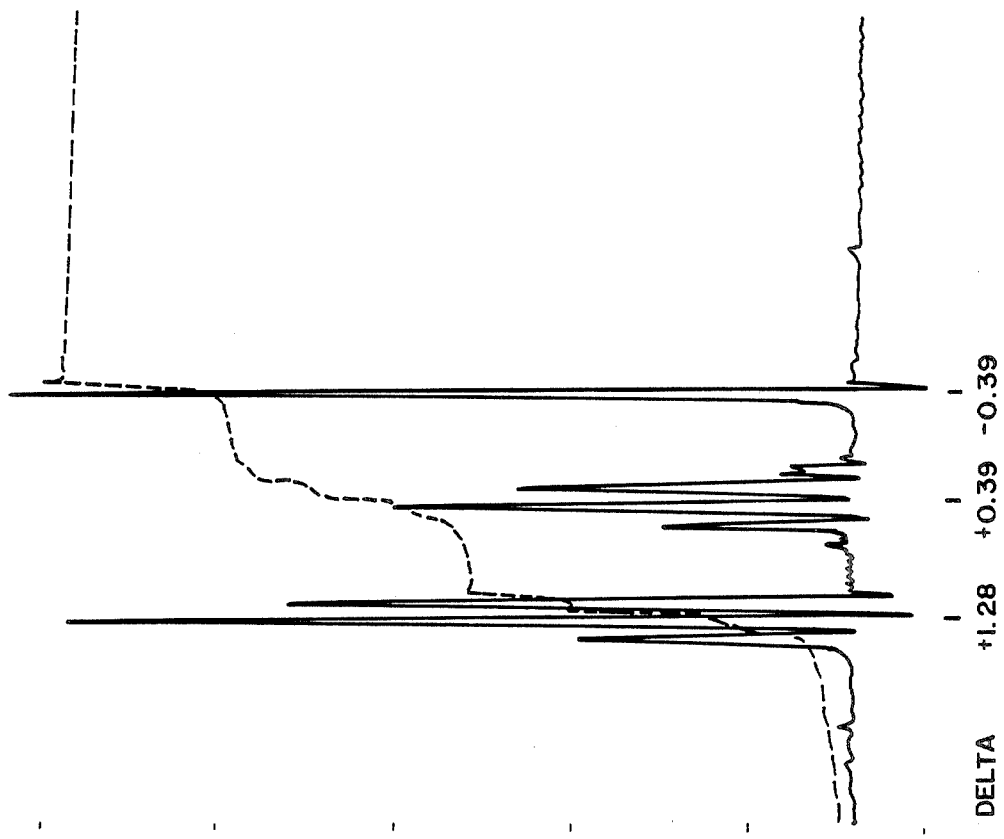
FIG. 4 is a proton nuclear magnetic resonance spectrum of diethylmethylindium.
Figure 3:
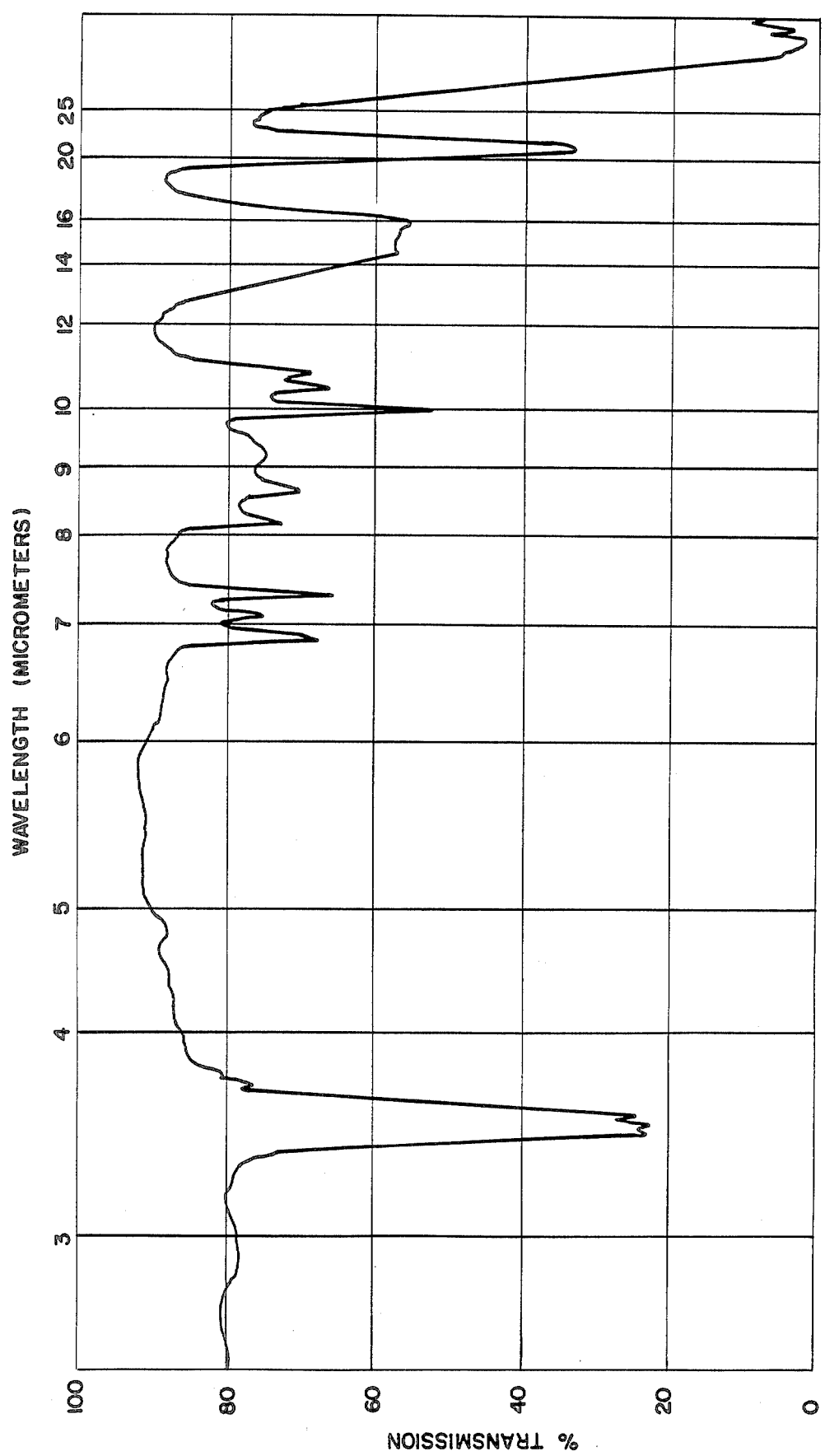
FIG. 3 is an infrared absorption spectrum of diethylmethylindium.

SYNTHESIS OF DIETHYLMETHYLINDIUM 5.00 ml. (6.30 g., 0.0312 mol.) of triethylindium was added to 2.495 g. (0.0156 mol.) of trimethylindium in a 50 ml. flask in a glove bag containing an argon atmosphere. The mixture was stirred overnight and then distilled at 33 to 35 degrees Celsius under full vacuum as previously defined. The distillate was a clear, colorless liquid. NMR and IR spectra were taken, and are provided as FIGS. 3 and 4 herein. The NMR is characterized by peaks at delta values of +1.28 (triplet ethyl); +0.39 (quartet ethyl); and −0.39 (singlet methyl). An integration of the areas under the peaks shows a ratio of ethyl to methyl of 1.94:1. The melting point was found to be below about 0 degrees Celsius, as the product failed to solidify when the container was placed in ice water.

EXAMPLE 4

PROPERTIES OF TRIMETHYLINDIUM AND TRIETHYLINDIUM (PRIOR ART)

Figure 5:
FIG. 5 is a proton nuclear magnetic resonance spectrum of trimethylindium, a prior art compound.

FIG. 5 is the NMR spectrum of trimethylindium, characterized by a singlet methyl peak at a delta value of −0.20. The melting point of trimethylindium is 88 degrees Celsius.

Figure 6:
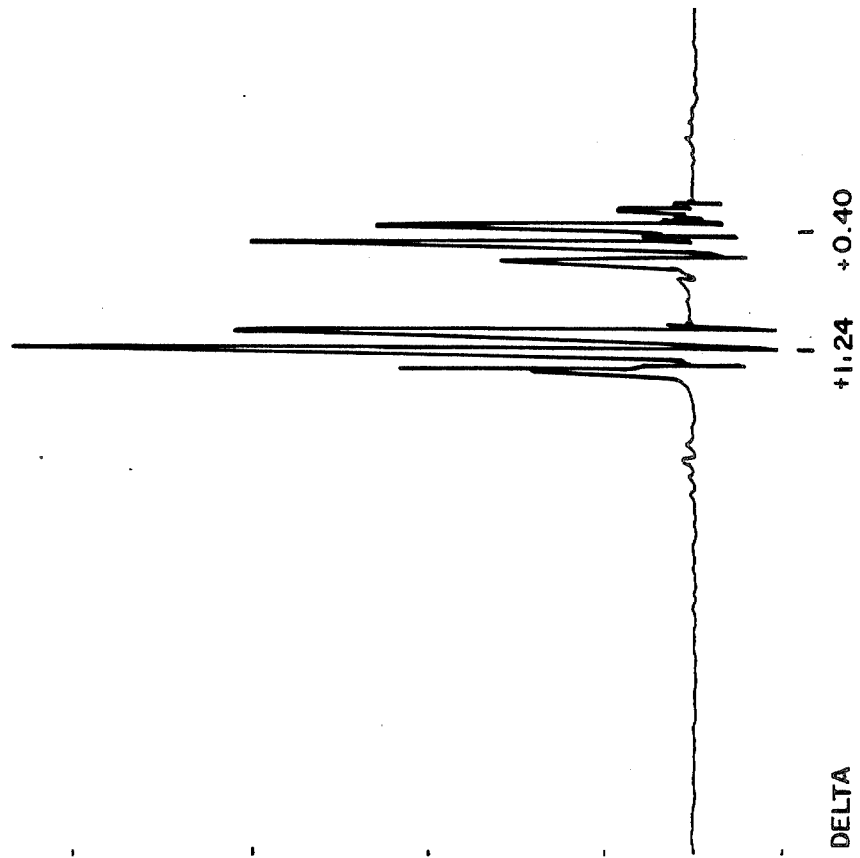
FIG. 6 is a proton nuclear magnetic resonance spectrum of triethylindium, a prior art compound.

FIG. 6 is the NMR spectrum of triethylindium, characterized by peaks at delta values of +1.24 (triplet ethyl) and +0.40 (quartet ethyl). The melting point of triethylindium is −32 degrees Celsius.

EXAMPLE 5

SYNTHESIS OF OTHER HYBRID ORGANOMETALLIC COMPOUNDS

Reactants 1 and 2 listed in Table III below are mixed in a flask in a glove bag under an argon atmosphere and stilled overnight. The hydrocarbon substituents of the reactants redistribute, thereby forming a mixture of materials which includes the product listed in Table III. The product is separated from other products and/or reactants by distillation.

TABLE III

| PRODUCT | REACTANT 1 | REACTANT 2 |
|---|---|---|
| $C_2H_5ZnCH_3$ | $(CH_3)_2Zn$ | $(C_2H_5)_2Zn$ |
| $CH_3CdC_2H_5$ | $(CH_3)_2Cd$ | $(C_2H_5)_2Cd$ |
| $CH_3HgC_6H_5$ | $(CH_3)_2Hg$ | $(C_6H_5)_2Hg$ |
| $(CH_3)_2BC_2H_5$ | $(CH_3)_3B$ | $(C_2H_5)_3B$ |
| $CH_3Al(C_6H_5)_2$ | $(CH_3)_3Al$ | $(C_6H_5)_3Al$ |
| $CH_3Al(C_6H_5CH_3)_2$ | $(CH_3)_3Al$ | $Al(C_6H_5CH_3)_3$ |
| $(CH_3)_2GaC_2H_5$ | $(CH_3)_3Ga$ | $(C_2H_5)_3Ga$ |
| $(CH_3)_2InC_2H_5$ | $(CH_3)_3In$ | $(C_2H_5)_3In$ |
| $(C_2H_5)_2InCH_3$ | $(CH_3)_3In$ | $(C_2H_5)_3In$ |
| $(CH_3)_2TlC_2H_5$ | $(CH_3)_3Tl$ | $(C_2H_5)_3Tl$ |
| $(C_4H_9)_2PC_6H_5$ | $(C_4H_9)_3P$ | $(C_6H_5)_3P$ |
| $(C_4H_9)PH(C_6H_5)$ | $(C_4H_9)_2PH$ | $(C_6H_5)_2PH$ |
| $(C_2H_5)_2As(CH_2C_6H_5)$ | $(C_2H_5)_3As$ | $As(CH_2C_6H_5)_3$ |
| $(CH_3)(C_4H_9)(C_6H_5)Sb$ | $(CH_3)_2(C_6H_5)Sb$ | $(C_4H_9)_3Sb$ |
| $CH_3Bi(CH_2CH_3CH_3)_2$ | $(CH_3)_3Bi$ | $(CH_3CH_2CH_2)_3Bi$ |
| $(CH_3)(C_2H_5)Se$ | $(CH_3)_2Se$ | $(C_2H_5)_2Se$ |
| $CH_3TeC_2H_5$ | $(CH_3)_2Te$ | $(C_2H_5)_2Te$ |
| $((CH_3)_2CHCH_2)CH_3AlH$ | $((CH_3)_2CHCH_2)_2AlH$ | $(CH_3)_3Al$ |
| $(C_2H_5)CH_3AsH$ | $(CH_3)_2AsH$ | $(C_2H_5)_3As$ |
| $(C_2H_5)SeH$ | $(C_2H_5)_2Se$ | $SeH_2$ |
| $(C_6H_5)MgCH_3$ | $(C_6H_5)_2Mg$ | $(CH_3)_2Mg$ |
| 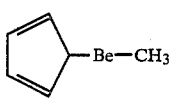 | 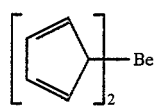 | $(CH_3)_2Be$ |

EXAMPLE 6

MOCVD PROCESS

Diethylarsine, prepared as described previously, is placed in a bubbler and suitably interconnected with a source of hydrogen gas and a deposition chamber. Trimethylgallium is placed in a second bubbler and suitably interconnected with a source of hydrogen gas and the same deposition chamber. A substrate is placed within the deposition chamber. Vapors of diethylarsine and trimethylgallium are transported into the deposition chamber, where they break down and react to form a gallium arsenide film on said substrate. The film is analyzed for carbon content and found to contain a reduced amount thereof, compared to the carbon content of a gallium arsenide film made under similar conditions, using trimethylgallium and arsine as reactants.

EXAMPLE 7

MOCVD PROCESS

Methyldiethylindium prepared as described previously is placed in a bubbler and suitably interconnected with a source of hydrogen gas and a deposition chamber. The chamber is also supplied with phosphine gas. The bubbler is maintained at 20 degrees Celsius using a suitable heat source, the deposition chamber is maintained at 650 degrees Celsius, and an indium phosphide substrate is supported within the deposition chamber. The entraining hydrogen is delivered at 100 cubic centimeters per minute (at standard temperature and pressure). The partial pressure of hydrogen in the deposition chamber is atmospheric pressure, and the partial pressure of methyldiethylindium is about 10 torrs, the partial pressure of phosphine being atmospheric pressure. After about 30 minutes of deposition, a coating of indium phosphide approximately 2 microns thick, uniform in composition and thickness, is found to be deposited on the substrate.

What is claimed is:

1. A compound having the structure:

$$\begin{array}{c} X-N-Y \\ | \\ H \end{array}$$

wherein H is hydride and the respective identities of N, X, and Y are selected from the following table of species:

| N | X | Y |
|---|---|---|
| arsenic | hydride | s-butyl |

-continued

| N | X | Y |
|---|---|---|
| arsenic | hydride | i-butyl |
| arsenic | hydride | n-pentyl |
| arsenic | hydride | i-pentyl |
| arsenic | hydride | t-pentyl |
| arsenic | hydride | neopentyl |
| arsenic | hydride | cyclopentadienyl |
| arsenic | methyl | i-propyl |
| arsenic | methyl | n-butyl |
| arsenic | methyl | s-butyl |
| arsenic | methyl | i-butyl |
| arsenic | methyl | t-butyl |
| arsenic | methyl | n-pentyl |
| arsenic | methyl | i-pentyl |
| arsenic | methyl | t-pentyl |
| arsenic | methyl | neopentyl |
| arsenic | methyl | cyclopentadienyl |
| arsenic | ethyl | n-propyl |
| arsenic | ethyl | i-propyl |
| arsenic | ethyl | n-butyl |
| arsenic | ethyl | s-butyl |
| arsenic | ethyl | i-butyl |
| arsenic | ethyl | t-butyl |
| arsenic | ethyl | n-pentyl |
| arsenic | ethyl | i-pentyl |
| arsenic | ethyl | t-pentyl |
| arsenic | ethyl | neopentyl |
| arsenic | ethyl | cyclopentadienyl |
| arsenic | ethyl | phenyl |
| arsenic | n-propyl | i-propyl |
| arsenic | n-propyl | n-butyl |
| arsenic | n-propyl | s-butyl |
| arsenic | n-propyl | i-butyl |
| arsenic | n-propyl | t-butyl |
| arsenic | n-propyl | n-pentyl |
| arsenic | n-propyl | i-pentyl |
| arsenic | n-propyl | t-pentyl |
| arsenic | n-propyl | neopentyl |
| arsenic | n-propyl | cyclopentadienyl |
| arsenic | n-propyl | phenyl |
| arsenic | i-propyl | n-butyl |
| arsenic | i-propyl | s-butyl |
| arsenic | i-propyl | i-butyl |
| arsenic | i-propyl | t-butyl |
| arsenic | i-propyl | n-pentyl |
| arsenic | i-propyl | i-pentyl |
| arsenic | i-propyl | t-pentyl |
| arsenic | i-propyl | neopentyl |
| arsenic | i-propyl | cyclopentadienyl |
| arsenic | i-propyl | phenyl |
| arsenic | n-butyl | s-butyl |
| arsenic | n-butyl | i-butyl |
| arsenic | n-butyl | t-butyl |
| arsenic | n-butyl | n-pentyl |
| arsenic | n-butyl | i-pentyl |
| arsenic | n-butyl | t-pentyl |
| arsenic | n-butyl | neopentyl |
| arsenic | n-butyl | cyclopentadienyl |
| arsenic | n-butyl | phenyl |
| arsenic | s-butyl | s-butyl |
| arsenic | s-butyl | i-butyl |
| arsenic | s-butyl | t-butyl |
| arsenic | s-butyl | n-pentyl |
| arsenic | s-butyl | i-pentyl |
| arsenic | s-butyl | t-pentyl |
| arsenic | s-butyl | neopentyl |
| arsenic | s-butyl | cyclopentadienyl |
| arsenic | s-butyl | phenyl |
| arsenic | i-butyl | i-butyl |
| arsenic | i-butyl | t-butyl |
| arsenic | i-butyl | n-pentyl |
| arsenic | i-butyl | i-pentyl |
| arsenic | i-butyl | t-pentyl |
| arsenic | i-butyl | neopentyl |
| arsenic | i-butyl | cyclopentadienyl |
| arsenic | i-butyl | phenyl |
| arsenic | t-butyl | n-pentyl |
| arsenic | t-butyl | i-pentyl |
| arsenic | t-butyl | t-pentyl |
| arsenic | t-butyl | neopentyl |
| arsenic | t-butyl | cyclopentadienyl |
| arsenic | t-butyl | phenyl |
| arsenic | n-pentyl | n-pentyl |
| arsenic | n-pentyl | i-pentyl |
| arsenic | n-pentyl | t-pentyl |
| arsenic | n-pentyl | neopentyl |
| arsenic | n-pentyl | cyclopentadienyl |
| arsenic | n-pentyl | phenyl |
| arsenic | i-pentyl | i-pentyl |
| arsenic | i-pentyl | t-pentyl |
| arsenic | i-pentyl | neopentyl |
| arsenic | i-pentyl | cyclopentadienyl |
| arsenic | i-pentyl | phenyl |
| arsenic | t-pentyl | t-pentyl |
| arsenic | t-pentyl | neopentyl |
| arsenic | t-pentyl | cyclopentadienyl |
| arsenic | t-pentyl | phenyl |
| arsenic | neopentyl | neopentyl |
| arsenic | neopentyl | cyclopentadienyl |
| arsenic | neopentyl | phenyl |
| arsenic | cyclopentadienyl | cyclopentadienyl |
| arsenic | cyclopentadienyl | phenyl |
| phosphorus | hydride | t-pentyl |
| phosphorus | hydride | neopentyl |
| phosphorus | methyl | s-butyl |
| phosphorus | methyl | i-butyl |
| phosphorus | methyl | t-butyl |
| phosphorus | methyl | n-pentyl |
| phosphorus | methyl | i-pentyl |
| phosphorus | methyl | t-pentyl |
| phosphorus | methyl | neopentyl |
| phosphorus | methyl | cyclopentadienyl |
| phosphorus | ethyl | n-propyl |
| phosphorus | ethyl | i-propyl |
| phosphorus | ethyl | n-butyl |
| phosphorus | ethyl | s-butyl |
| phosphorus | ethyl | i-butyl |
| phosphorus | ethyl | t-butyl |
| phosphorus | ethyl | n-pentyl |
| phosphorus | ethyl | i-pentyl |
| phosphorus | ethyl | t-pentyl |
| phosphorus | ethyl | neopentyl |
| phosphorus | ethyl | cyclopentadienyl |
| phosphorus | n-propyl | i-propyl |
| phosphorus | n-propyl | n-butyl |
| phosphorus | n-propyl | s-butyl |
| phosphorus | n-propyl | i-butyl |
| phosphorus | n-propyl | t-butyl |
| phosphorus | n-propyl | n-pentyl |
| phosphorus | n-propyl | i-pentyl |
| phosphorus | n-propyl | t-pentyl |
| phosphorus | n-propyl | neopentyl |
| phosphorus | n-propyl | cyclopentadienyl |
| phosphorus | n-propyl | phenyl |
| phosphorus | i-propyl | n-butyl |
| phosphorus | i-propyl | s-butyl |
| phosphorus | i-propyl | t-butyl |
| phosphorus | i-propyl | n-pentyl |
| phosphorus | i-propyl | i-pentyl |
| phosphorus | i-propyl | t-pentyl |
| phosphorus | i-propyl | neopentyl |
| phosphorus | i-propyl | cyclopentadienyl |
| phosphorus | i-propyl | phenyl |
| phosphorus | n-butyl | s-butyl |
| phosphorus | n-butyl | i-butyl |
| phosphorus | n-butyl | t-butyl |
| phosphorus | n-butyl | n-pentyl |
| phosphorus | n-butyl | i-pentyl |
| phosphorus | n-butyl | t-pentyl |
| phosphorus | n-butyl | neopentyl |
| phosphorus | n-butyl | cyclopentadienyl |
| phosphorus | s-butyl | i-butyl |
| phosphorus | s-butyl | t-butyl |
| phosphorus | s-butyl | n-pentyl |
| phosphorus | s-butyl | i-pentyl |
| phosphorus | s-butyl | t-pentyl |
| phosphorus | s-butyl | neopentyl |
| phosphorus | s-butyl | cyclopentadienyl |
| phosphorus | s-butyl | phenyl |
| phosphorus | i-butyl | t-butyl |
| phosphorus | i-butyl | n-pentyl |
| phosphorus | i-butyl | i-pentyl |
| phosphorus | i-butyl | t-pentyl |

-continued

| N | X | Y |
|---|---|---|
| phosphorus | i-butyl | neopentyl |
| phosphorus | i-butyl | cyclopentadienyl |
| phosphorus | i-butyl | phenyl |
| phosphorus | t-butyl | n-pentyl |
| phosphorus | t-butyl | t-pentyl |
| phosphorus | t-butyl | neopentyl |
| phosphorus | t-butyl | cyclopentadienyl |
| phosphorus | n-pentyl | n-pentyl |
| phosphorus | n-pentyl | i-pentyl |
| phosphorus | n-pentyl | t-pentyl |
| phosphorus | n-pentyl | neopentyl |
| phosphorus | n-pentyl | cyclopentadienyl |
| phosphorus | n-pentyl | phenyl |
| phosphorus | i-pentyl | t-pentyl |
| phosphorus | i-pentyl | neopentyl |
| phosphorus | i-pentyl | cyclopentadienyl |
| phosphorus | i-pentyl | phenyl |
| phosphorus | t-pentyl | t-pentyl |
| phosphorus | t-pentyl | neopentyl |
| phosphorus | t-pentyl | cyclopentadienyl |
| phosphorus | t-pentyl | phenyl |
| phosphorus | neopentyl | neopentyl |
| phosphorus | neopentyl | cyclopentadienyl |
| phosphorus | neopentyl | phenyl |
| phosphorus | cyclopentadienyl | cyclopentadienyl |

2. The compound of claim 1, where N is arsenic, X is hydride, Y is selected from s-butyl and i-butyl.

3. The compound of claim 1, where N is arsenic, X is hydride, Y is pentyl.

4. The compound of claim 1, where N is arsenic, X is hydride, Y is cyclopentadienyl.

5. The compound of claim 1, where N is arsenic, X is methyl, Y is isopropyl.

6. The compound of claim 1, where N is arsenic, X is methyl, Y is butyl.

7. The compound of claim 1, where N is arsenic, X is methyl, Y is pentyl.

8. The compound of claim 1, where N is arsenic, X is methyl, Y is cyclopentadienyl.

9. The compound of claim 1, where N is arsenic, X is ethyl, Y is propyl.

10. The compound of claim 1, where N is arsenic, X is ethyl, Y is butyl.

11. The compound of claim 1, where N is arsenic, X is ethyl, Y is pentyl.

12. The compound of claim 1, where N is arsenic, X is ethyl, Y is cyclopentadienyl.

13. The compound of claim 1, where N is arsenic, X is ethyl, Y is phenyl.

14. The compound of claim 1, where N is arsenic, X is n-propyl, Y is isopropyl.

15. The compound of claim 1, where N is arsenic, X is propyl, Y is butyl.

16. The compound of claim 1, where N is arsenic, X is propyl, Y is pentyl.

17. The compound of claim 1, where N is arsenic, X is propyl, Y is cyclopentadienyl.

18. The compound of claim 1, where N is arsenic, X is propyl, Y is phenyl.

19. The compound of claim 1, where N is arsenic, X is butyl, Y is isobutyl.

20. The compound of claim 1, where N is arsenic, X is butyl, Y is sec-butyl.

21. The compound of claim 1, where N is arsenic, X is butyl, Y is pentyl.

22. The compound of claim 1, where N is arsenic, X is butyl, Y is cyclopentadienyl.

23. The compound of claim 1, where N is arsenic, X is butyl, Y is phenyl.

24. The compound of claim 1, where N is arsenic, X is pentyl, Y is pentyl.

25. The compound of claim 1, where N is arsenic, X is pentyl, Y is cyclopentadienyl.

26. The compound of claim 1, where N is arsenic, X is pentyl, Y is phenyl.

27. The compound of claim 1, where N is arsenic, X is cyclopentadienyl, Y is cyclopentadienyl.

28. The compound of claim 1, where N is arsenic, X is cyclopentadienyl, Y is phenyl.

29. The compound of claim 1, where N is phosphorus, X is methyl, Y is selected from s-butyl, i-butyl, and t-butyl.

30. The compound of claim 1, where N is phosphorus, X is methyl, Y is pentyl.

31. The compound of claim 1, where N is phosphorus, X is methyl, Y is cyclopentadienyl.

32. The compound of claim 1, where N is phosphorus, X is ethyl, Y is propyl.

33. The compound of claim 1, where N is phosphorus, X is ethyl, Y is butyl.

34. The compound of claim 1, where N is phosphorus, X is ethyl, Y is pentyl.

35. The compound of claim 1, where N is phosphorus, X is ethyl, Y is cyclopentadienyl.

36. The compound of claim 1, where N is phosphorus, X is propyl, Y is pentyl.

37. The compound of claim 1, where N is phosphorus, X is propyl, Y is cyclopentadienyl.

38. The compound of claim 1, where N is phosphorus, X is propyl, Y is phenyl.

39. The compound of claim 1, where N is phosphorus, X is butyl, Y is pentyl.

40. The compound of claim 1, where N is phosphorus, X is butyl, Y is cyclopentadienyl.

41. The compound of claim 1, where N is phosphorus, X is pentyl, Y is cyclopentadienyl.

42. The compound of claim 1, where N is phosphorus, X is pentyl, Y is phenyl.

43. The compound of claim 1, where N is phosporus, X is cyclopentadienyl, Y is cyclopentadienyl.

* * * * *